United States Patent [19]

Ruff et al.

[11] Patent Number: 5,446,026
[45] Date of Patent: Aug. 29, 1995

[54] POTENT NON-OPIATE ANALGESIC

[75] Inventors: Michael R. Ruff, Potomac; Joanna M. Hill, Gaithersburg; Lawrence D. Kwart, Germantown; Candace B. Pert, Potomac, all of Md.

[73] Assignee: Advanced Peptides & Biotechnology Sciences, Sewickley, Pa.

[21] Appl. No.: 19,830

[22] Filed: Feb. 19, 1993

Related U.S. Application Data

[63] Continuation of Ser. No. 850,141, Mar. 12, 1992, abandoned, which is a continuation of Ser. No. 541,199, Jun. 11, 1990, abandoned, which is a continuation of Ser. No. 391,272, Aug. 9, 1989, abandoned.

[51] Int. Cl.$^6$ ............................ C07K 7/06; C07K 9/00
[52] U.S. Cl. ............................................ 514/15; 514/8; 530/307; 530/322; 530/328
[58] Field of Search .................. 514/15, 8; 530/307, 530/328, 322

[56] References Cited

U.S. PATENT DOCUMENTS 4,239,680 12/1980 Hughes et al. ............... 530/307
4,764,591 8/1988 Orlowski et al. ............. 530/307

OTHER PUBLICATIONS

Koida et al. *Chem. Abstracts.* 1983. vol. 98, p. 128.
Bourgoin et al. *Eur. J. of Pharmacol.* 1988. vol. 156, pp. 13–14, 20–21.

*Primary Examiner*—Lester L. Lee
*Attorney, Agent, or Firm*—Cobrin Gittes & Samuel

[57] ABSTRACT

The present invention is directed to Cholic, Chenodeoxycholic and deoxycholic acid derivatives of a peptide having the sequence: Pro-Arg-Thr-Asn-Thr-Gly-Ser-Gly-Thr-Pro-amide and use thereof in inducing analgesia.

11 Claims, 7 Drawing Sheets

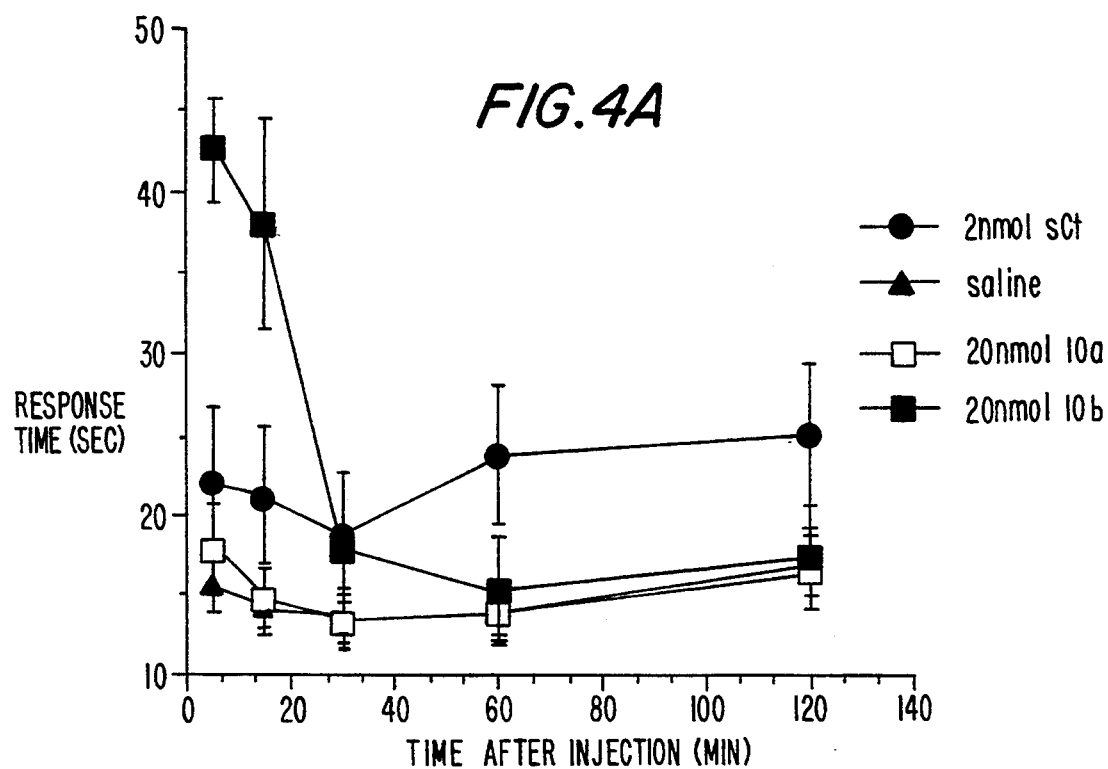
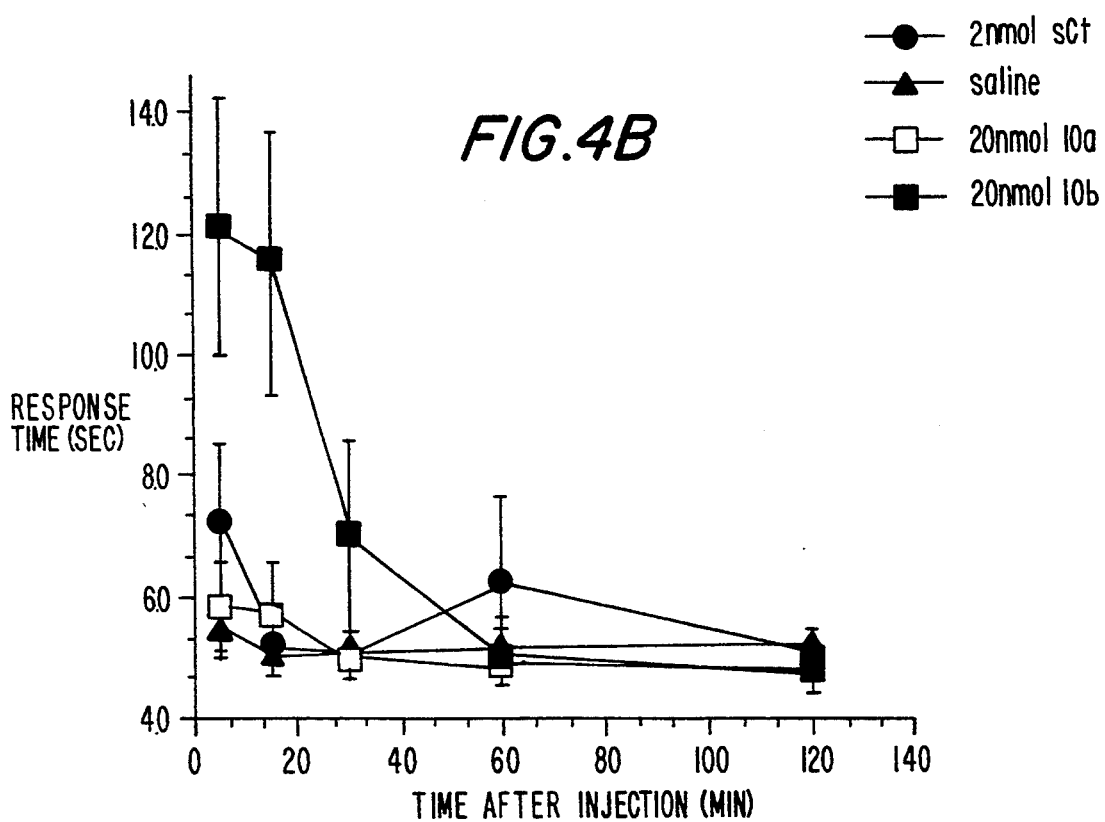

POTENT NON-OPIATE ANALGESIC

This application is a continuation of application Ser. No. 07/850,141, filed Mar. 12, 1992, which is a continuation of application Ser. No. 07/541,199, filed Jun. 11, 1990, which is a continuation of Ser. No. 07/391,272, filed Aug. 9, 1989 all now abandoned.

"No drug acts unless it is fixed" is the prime tenet of pharmacology. These sites where drug is fixed are called "receptors;" they are generally cell surface molecules whose subtle transition in shape upon binding with drug induces changes in the cell's function by altering ion flux and/or the second messenger cascade. The brain and body use a network of these receptors and "messenger molecules" (usually peptide in nature) to modulate and integrate all physiological functions from digestion to perception. Peptide Design is expert in all technologies related to peptides and their receptors including visualization by autoradiography of the distribution pattern of receptors through the brain and body, direct radioreceptor binding assays, electrophoretic separation of receptor molecules, and use of computer-assisted database analyses to deduce short peptide sequences likely to have potent bioactivity.

Calcitonin is a 32 amino acid peptide secretion of the parathyroid gland, well known for its ability to induce calcium influx into bone and thus prevent or reverse osteoporosis. Less well appreciated, however, is the fact that calcitonin is an extremely potent analgesic not only in rats but also in terminal cancer patients with chronic intractable pain. No important side effects were observed in any of the patients in the human study, but administration was by inconvenient injection into the subarachnoid space of the spinal cord because calcitonin does not penetrate into the brain. Our strategy was to deduce which shorter fragment of the calcitonin sequence was responsible for receptor binding, and modify it appropriately to insure proper pharmacokinetics (entry into the brain without biodegradation by ubiquitous proteolytic enzymes). The literature already showed that the calcitonin receptor is unrelated to the opiate receptor with a different brain distribution pattern, being almost exclusively confined to the core of the brain stem where analgesic activity has been shown to be mediated. Moreover, cross competition experiments, cross tolerance experiments, and electrophoretic molecular receptor analysis carried out in our own laboratory shows that the calcitonin receptor is a discrete molecular entity with a molecular weight of 69 Kd unlike the opiate receptor which appears to be a 58 Kd doublet.

It should be noted that the periaqueductal gray region of rat and human brain is an area mediating pain thresholds in the lower brain stem surrounding the third ventricle which contains dense clusters of receptors for calcitonin (FIG. 1). Thus, our goal was to use our expertise and technology to develop a potent non addictive analgesic of a new (non-opiate) class based upon the calcitonin structure. Many pharmaceutical companies in the past have underestimated the bioactivity of peptides by obtaining "false negative" data by having access only to in vivo bioassays where destruction of proteasesensitive peptides often occurs before receptor occupation. Not only do out in vitro bioassays prevent this problem, but we were able to perform in vivo rodent analgesia testing initially through an indwelling cannula aimed directly at calcitonin receptor sites in the periaqueductal gray. It should be noticed that the first experiments with enkephalin, the endogenous brain morphine-like peptide, gave only weak and transient (gone in seconds) analgesia even after similar periaqueductal gray administration. Only after subsequent peptide modification with D-ala was long-lasting analgesia demonstrated.

BRIEF DESCRIPTION OF THE DRAWINGS

FIG. 4A is a graph showing analgesia (hot plate test) comparing response time (in seconds) from time following drug administration (in minutes);

FIG. 4B is a graph showing similar analgesia using a paw pressure test;

DESCRIPTION OF THE INVENTION

The peptide of our invention is Pro-Arg-Thr-Asn-Thr-Gly-Ser-Gly-Thr-Pro-NH$_2$. The invention includes the peptide itself, methods of using this peptide to attain analgesia and pharmaceutical compositions containing this peptide. The peptide is sometimes identified herein and in the attached drawings (for convenience) by its code name PD 89.0106.

Figure 1:
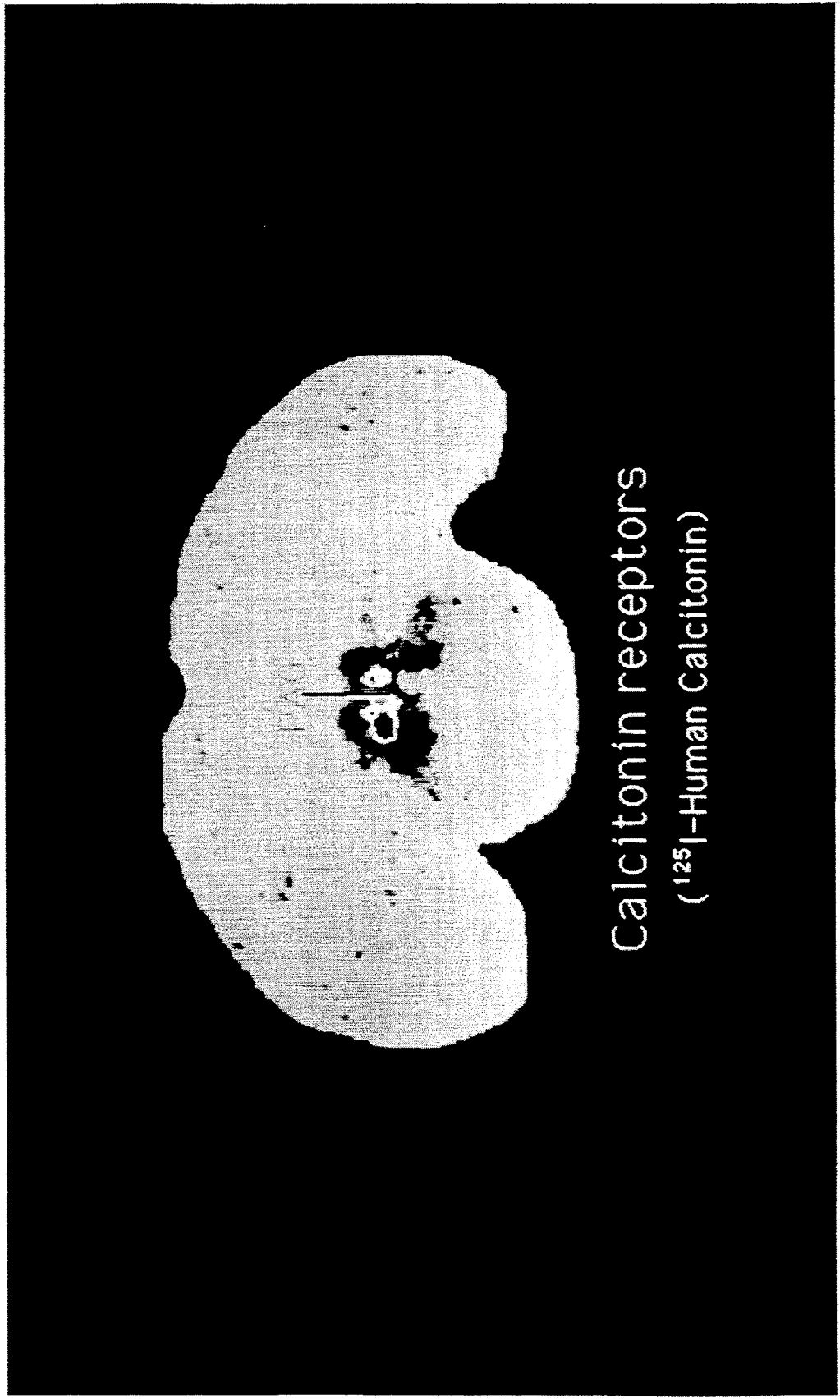
FIG. 1 is an autoradiograph of a cross section of a rat lower brain stem illustrating the clusters for receptors of calcitonin.
Figure 2A:
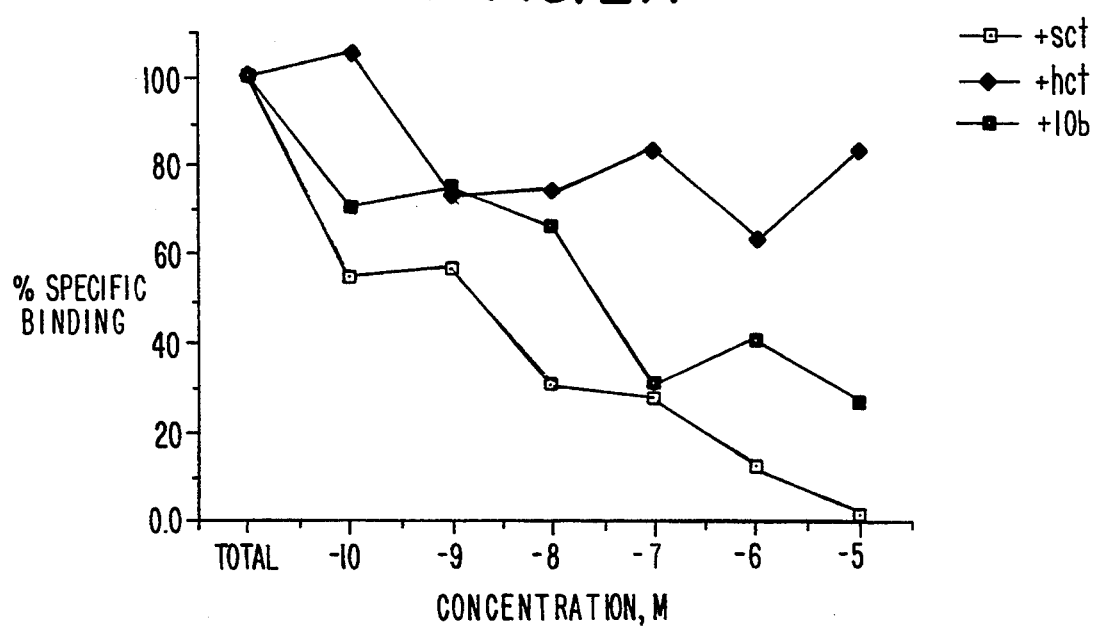
FIGS. 2A and 2B are graphs showing the specific binding of the novel peptide as a function of displacement of 125-I human calcitonin (2A) and 125I salmon calcitonin (2B)
Figure 2B:
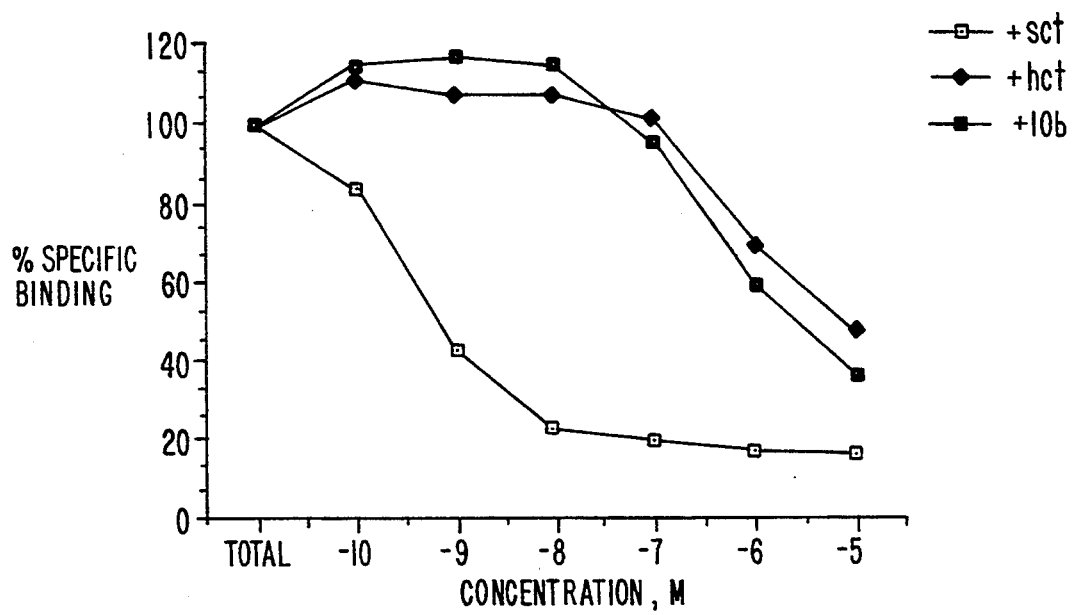
Figure 3A:
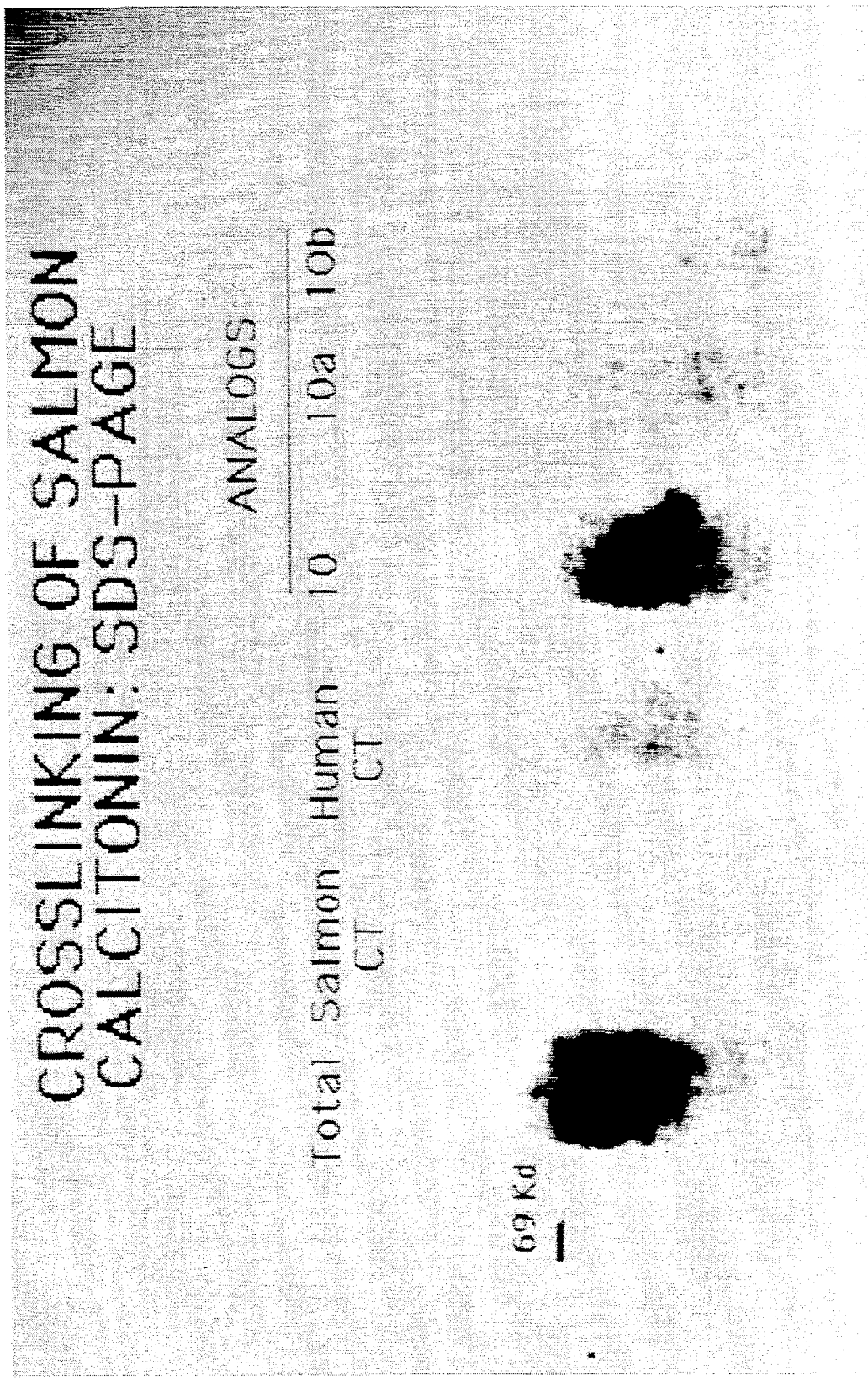
FIGS. 3A and 3B are photographs of SDS-PAGE gels showing the crosslinking and in vitro receptor binding of the novel peptide with salmon calcitonin (3A) and human calcitonin (3B)
Figure 3B:
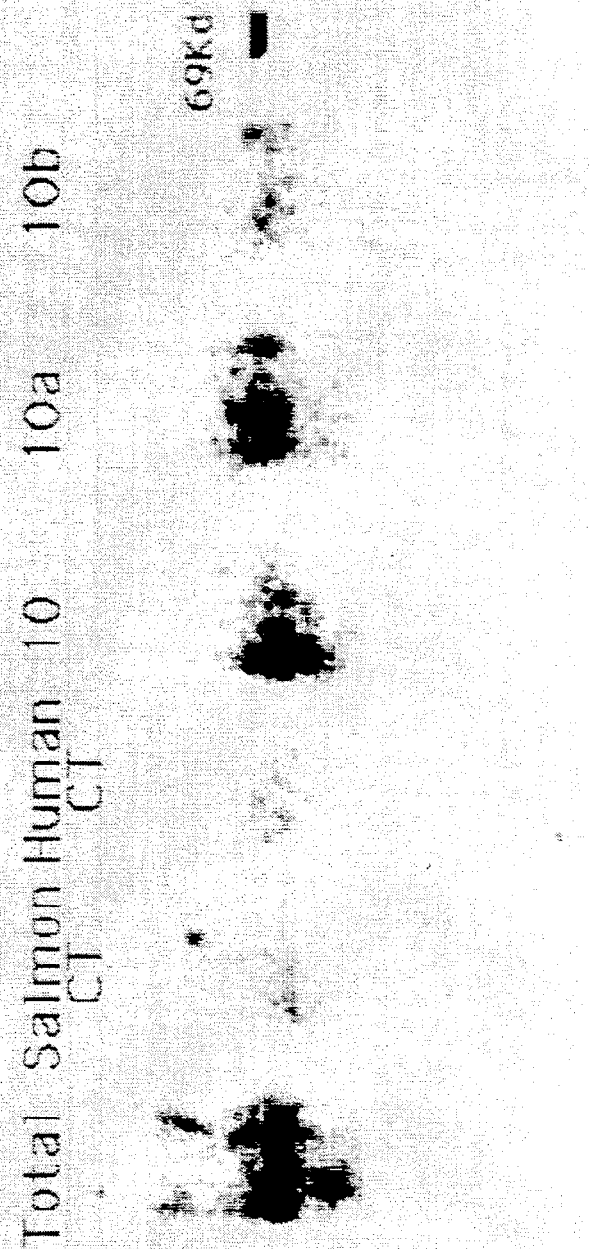
Figure 4C:
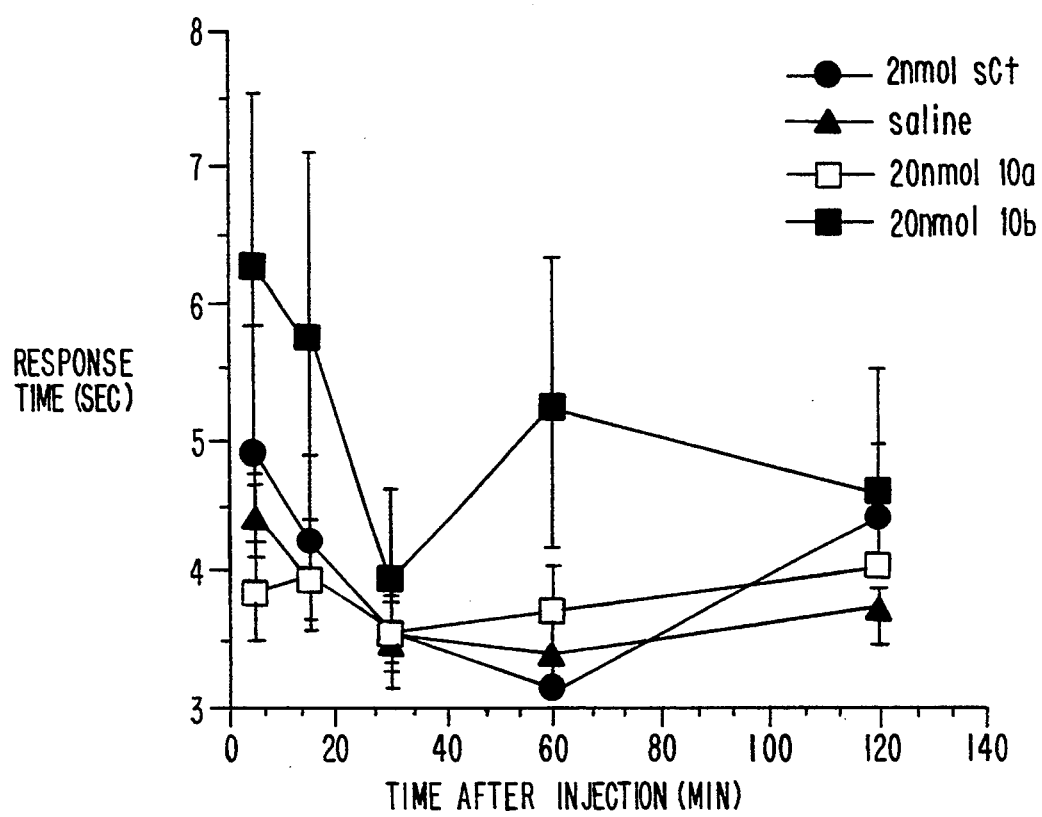
FIG. 4C is a graph showing similar analgesia in a tail flick test.
Figure 5A:
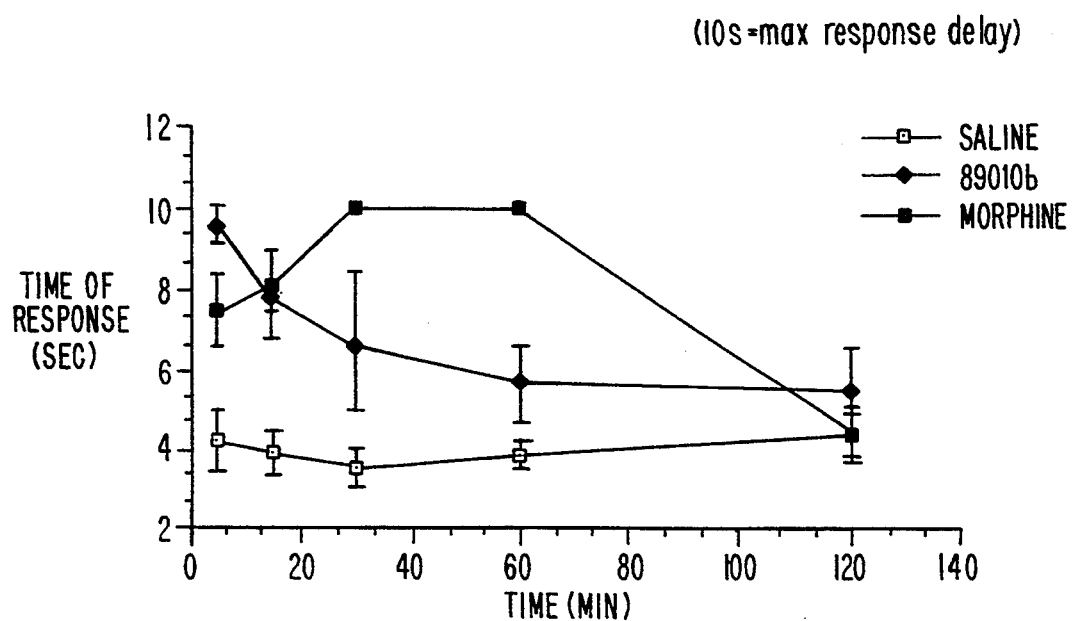
FIGS. 5A and 5B are graphs comparing the analgesic effect of a subcutaneous injection again measuring the time for response (in seconds) against duration of effect (in minutes) using tail flick and hot plate tests, respectively.
Figure 5B:
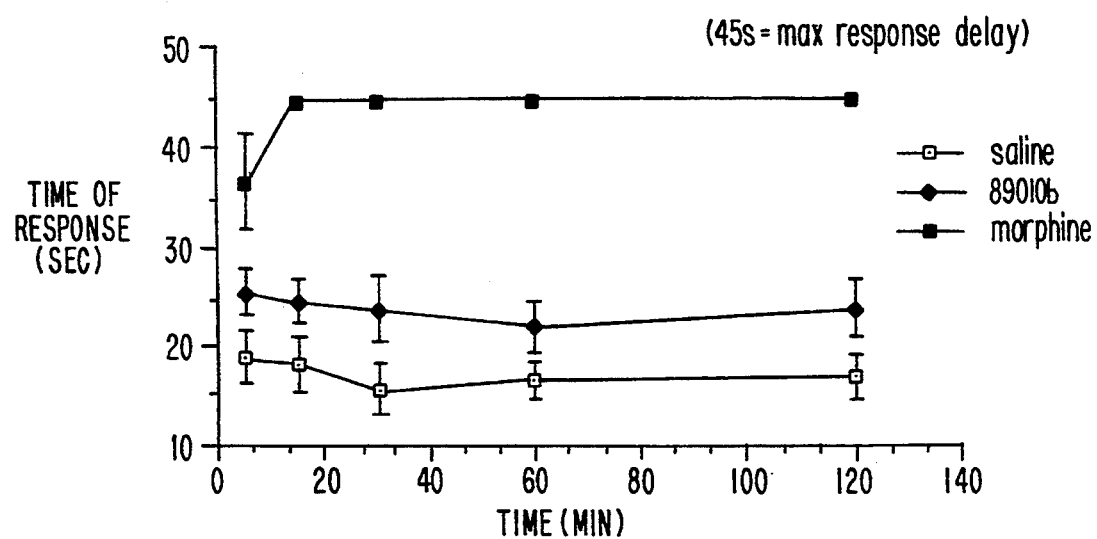

We have developed a modified calcitonin decapeptide which (1) appears to be a potent human calcitonin and weak salmon calcitonin analog by in vitro receptor binding (FIG. 2); (2) at 1 µM (FIG. 3) it completely displaces both Iodinated salmon and human calcitonin from the 69 Kd receptor molecule. (3) PD89.010b appeared to give significant and profound analgesic responses in three classical tests of rodent analgesia which also respond to morphine (FIG. 4). FIG. 5 showed that upon subcutaneous injection of only one quarter the molar equivalent of morphine, PD89.010b resulted in profound and long lived analgesia in both the tail-flick and hot plate tests. Notice that the Peptide Design compound has a much more rapid onset of analgesia than the much more hydrophyllic opiate. Moreover at two hours, the last time point tested the Peptide Design compound still is showing significant analgesia whereas morphine has already returned to baseline suggesting a potentially longer duration of action than morphine which is in fact consistent with the human studies of the whole calcitonin molecule.

Not only did this compound show profound and potent long lasting analgesia of an opiate quality (without acting through opiate, addictive mechanisms), but PD89.010b appeared to trained observers of rodent behavior to have no obvious behavioral incapacitation effects. Both the righting reflex and behavior and balance on an inclined plane remained unchanged suggesting that there was no obvious motor or neurological side effects with this compound. Studies of analgesia in monkeys is underway and following animal toxicity human trials should be undertaken. This compound does not appear to enhance uptake of calcium into bone under the conditions tested in which salmon calcitonin gave a profound response. We would expect that this peptide, like other peptide analogs of naturally occurring modulatory substances, would be potent in quite low (milligram) doses in humans and should be able to alleviate quite severe pain even in these low doses.

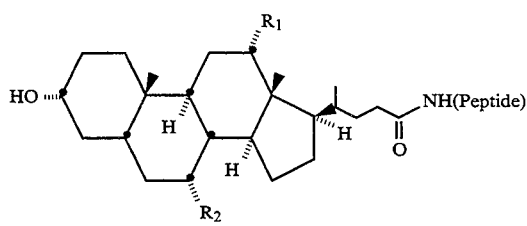

$R_1$, $R_2$=OH: Cholic Acid 89.010a $R_1$=H, $R_2$=OH: Chenodeoxycholic Acid 89.010b $R_1$=OH, $R_2$=H: Deoxycholic Acid

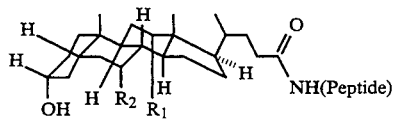

PEPTIDE-Pro-Arg-Thr-Asn-Thr-Gly-Ser-Gly-Thr-Pro-amide.

What is claimed is:

1. A peptide of the formula

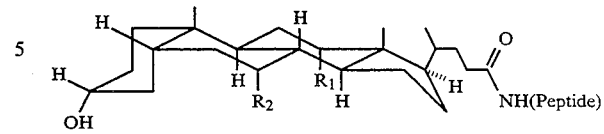

wherein the peptide fragment has the following amino acid sequence Pro-Arg-Thr-Asn-Thr-Gly-Ser-Gly-Thr-Pro-amide and wherein $R_1$ and $R_2$ are selected from the group consisting of hydrogen and hydroxyl.

2. The peptide of claim 1 wherein $R_1$ and $R_2$ are both hydroxyl.

3. The peptide of claim 1 wherein $R_1$ is hydrogen and $R_2$ is hydroxyl.

4. The peptide of claim 1 wherein $R_1$ is hydroxyl and $R_2$ is hydrogen.

5. The peptide of claim 2 being a cholic acid derivative.

6. The peptide of claim 3 being a chenodeoxycholic acid derivative.

7. The peptide of claim 4 being a deoxychloic acid derivative.

8. A pharmaceutical composition comprising the peptide of claim 1 and a pharmaceutical acceptable carrier or diluent.

9. The composition of claim 8 wherein $R_1$ is hydrogen and $R_2$ is hydroxyl.

10. A method of inducing analgesia in a patient comprising administering to a patient in need of the same an effective analgesic amount of the peptide of claim 1.

11. The method of claim 10 wherein $R_1$ is hydrogen and $R_2$ is hydroxyl.

* * * * *